(12) United States Patent
Muraki

(10) Patent No.: US 9,669,403 B2
(45) Date of Patent: Jun. 6, 2017

(54) MICROPARTICLE MEASUREMENT DEVICE AND LIQUID DELIVERY METHOD IN MICROPARTICLE MEASUREMENT DEVICE

(71) Applicant: Sony Corporation, Tokyo (JP)

(72) Inventor: Yosuke Muraki, Tokyo (JP)

(73) Assignee: Sony Corporation, Tokyo (JP)

( * ) Notice: Subject to any disclaimer, the term of this patent is extended or adjusted under 35 U.S.C. 154(b) by 456 days.

(21) Appl. No.: 14/239,794

(22) PCT Filed: Jun. 10, 2013

(86) PCT No.: PCT/JP2013/065961
§ 371 (c)(1),
(2) Date: Feb. 20, 2014

(87) PCT Pub. No.: WO2014/017186
PCT Pub. Date: Jan. 30, 2014

(65) Prior Publication Data
US 2014/0208875 A1    Jul. 31, 2014

(30) Foreign Application Priority Data
Jul. 25, 2012 (JP) ................................. 2012-165167

(51) Int. Cl.
*G01N 15/02* (2006.01)
*B01L 3/00* (2006.01)
(Continued)

(52) U.S. Cl.
CPC .......... *B01L 3/502* (2013.01); *G01N 15/1404* (2013.01); *G01N 15/1459* (2013.01);
(Continued)

(58) Field of Classification Search
None
See application file for complete search history.

(56) References Cited

U.S. PATENT DOCUMENTS 4,683,212 A * 7/1987 Uffenheimer ................... 436/52
8,124,725 B2 * 2/2012 Marino et al. ................ 530/324
(Continued)

FOREIGN PATENT DOCUMENTS

JP    09-139334        5/1997
JP    09-139334 A      5/1997
(Continued)

OTHER PUBLICATIONS

Office Action for JP Patent Application No. 2013-556441, issued on Feb. 28, 2017, 4 pages.

*Primary Examiner* — Robert R Raevis
(74) *Attorney, Agent, or Firm* — Chip Law Group

(57) ABSTRACT

Provided is a microparticle measurement device that can deliver a liquid that is used in the analysis of microparticles in a stable manner. The microparticle measurement device includes a plurality of first tank units to which a liquid is supplied from the outside, and which are respectively arranged in parallel, and a bulb unit that is connected to the plurality of first tank units, and which switches to a state in which it is possible to deliver the liquid to a flow channel through which microparticles flow. According to this microparticle measurement device, in addition to performing liquid delivery from a portion of first tank units, in which the replenishment of liquid has been completed, to a flow channel, it is possible to supply liquid from the outside to first tank units other than the first tank units that are delivering liquid.

9 Claims, 5 Drawing Sheets

(51) Int. Cl.
    *G01N 15/10*        (2006.01)
    *G01N 15/14*        (2006.01)
(52) U.S. Cl.
    CPC .............. *G01N 2015/1006* (2013.01); *G01N 2015/1409* (2013.01); *G01N 2015/149* (2013.01); *G01N 2015/1413* (2013.01)

(56) References Cited

U.S. PATENT DOCUMENTS

| | | | |
|---|---|---|---|
| 8,767,212 B2 * | 7/2014 | Kanda et al. | 356/442 |
| 2007/0121114 A1 * | 5/2007 | Berry et al. | 356/442 |
| 2013/0256136 A1 | 10/2013 | Muraki et al. | |
| 2013/0258075 A1 | 10/2013 | Muraki et al. | |
| 2013/0343149 A1 * | 12/2013 | Fox et al. | 366/138 |
| 2014/0144817 A1 | 5/2014 | Hashimoto et al. | |
| 2014/0193059 A1 | 7/2014 | Muraki | |

FOREIGN PATENT DOCUMENTS

| | | |
|---|---|---|
| JP | 09-288053 | 11/1997 |
| JP | 2003-302330 A | 10/2003 |
| JP | 2004-077484 | 3/2004 |
| JP | 2004-077484 A | 3/2004 |
| JP | 2009-539678 A | 11/2009 |
| JP | 2010-190680 | 9/2010 |
| JP | 2010-271168 | 12/2010 |
| JP | 2010-271168 A | 12/2010 |

\* cited by examiner

MICROPARTICLE MEASUREMENT DEVICE AND LIQUID DELIVERY METHOD IN MICROPARTICLE MEASUREMENT DEVICE

TECHNICAL FIELD

The present technology relates to a microparticle measurement device and a liquid delivery method in a microparticle measurement device. More specifically, the technology relates to a microparticle measurement device or the like in which it is possible to deliver a liquid to a flow channel through which microparticles flow in a stable manner.

BACKGROUND ART

Microparticle measurement devices (for example, a flow cytometer) that detect the characteristics of microparticles such as cells through optical, electrical or magnetic means, and only separate and recover microparticles that have specific characteristics are known.

For example, as a microchip type flow cytometer, PTL 1 discloses a "microparticle measurement device that is provided with a microchip on which a flow channel through which a liquid that contains microparticles flows, and an orifice through which the liquid that flows through the flow channel is ejected into a space outside the chip, are arranged, a vibration element for converting liquid in the orifice into liquid droplets and discharging the liquid droplets, charging means for applying an electric charge to the discharged liquid droplets, optical detection means that detect the optical characteristics of microparticles that flow through the flow channel, a pair of electrodes that are arranged to face one another along a movement direction of liquid droplets discharged into a space outside the chip with the liquid droplets that move interposed therebetween, and two or more containers that recover liquid droplets that pass between the pair of electrodes".

The liquid delivery of a liquid that is used by a microparticle measurement device to a flow channel is performed using a sample liquid tank that accommodates a sample liquid that includes microparticles, a sheath liquid tank that accommodates a sheath liquid, a liquid delivery pump that is used to deliver these liquids to the flow channel and the like (for example, refer to PTL 2).

CITATION LIST

Patent Literature

PTL 1: Japanese Unexamined Patent Application Publication No. 2010-190680
PTL 2: Japanese Unexamined Patent Application Publication No. 2010-271168

SUMMARY OF INVENTION

Technical Problem

In microparticle measurement devices, there are cases in which the formation of the liquid droplets that include microparticles and are ejected from the microchip becomes unstable when the sheath liquid is delivered from the tank to the flow channel. This accompanies changes in the residual quantity of sheath liquid (liquid level) inside the tank, and can occur as a result of pressure changes inside the tank due to the pump becoming large. Therefore, there is a problem in that there are cases in which it is not possible to deliver the sheath liquid to the flow channel in a stable manner.

In such a case, an object of the present technology is to provide a microparticle measurement device that can deliver a liquid that is used in the analysis of microparticles in a stable manner.

Solution to Problem

In order to solve the abovementioned problem, the present technology provides a microparticle measurement device including a plurality of first tank units to which a liquid is supplied from the outside, and which are respectively connected in parallel, and a bulb unit that is connected to the plurality of first tank units, and which switches to a state in which it is possible to deliver the liquid to a flow channel through which microparticles flow.

Since the microparticle measurement device is provided with a plurality of first tank units which are respectively connected in parallel, and a bulb unit that is connected to the plurality of first tank units, in addition to performing liquid delivery from a portion of the first tank units, in which the replenishment of liquid has been completed, to a flow channel, it is possible to supply liquid from the outside to first tank units other than the abovementioned first tank units that are delivering liquid.

The plurality of first tank units may be connected to a second tank unit that is on the outside, and a configuration in which the liquid is supplied from the second tank unit may be adopted.

The microparticle measurement device may further include a supply pump unit that supplies the liquid from the second tank unit to the plurality of first tank units.

The microparticle measurement device may be configured as a device in which the bulb unit and the supply pump unit are driven in conjunction.

The microparticle measurement device may be configured to be provided with the single bulb unit and the single supply pump unit.

Among the plurality of first tank units, the supply pump unit may cease the supply of the liquid to first tank units which are in a liquid delivery state with respect to the flow channel, and may supply the liquid to first tank units which are in a ceased liquid delivery state with respect to the flow channel.

The microparticle measurement device may further include a filter unit in a liquid delivery channel of the liquid between the bulb unit and the flow channel.

In the microparticle measurement device, the first tank unit may be provided inside the device.

In the microparticle measurement device, the flow channel may be configured as a channel that is provided on a microchip.

In addition, the present technology also provides a liquid delivery method in a microparticle measurement device, including setting a portion of tank units to a state in which the liquid is delivered to a flow channel through which microparticles flow using a bulb unit, among a plurality of first tank units to which a liquid is supplied from the outside, and which are respectively connected in parallel; setting tank units other than the portion of tank units to a state in which liquid delivery of the liquid to the flow channel is ceased; and supplying the liquid to the tank units other than the portion of tank units from the outside during a period when the liquid is being delivered from the portion of tank units to the flow channel.

In the present technology, "microparticles" can include a wide range of particles such as biologically-relevant microparticles such as cells, microorganisms, liposomes and the like, or synthetic particles such as latex particles and gel particles, and industrial particles.

Biologically-relevant microparticles can include chromosomes, liposomes, mitochondria, organelles (cell organelles) and the like that configure various cells. Cells can include animal cells (hematopoietic cells and the like) and plant cells. Microorganisms can include bacteria such as *Escherichia coli*, viruses such as tobacco mosaic virus, fungi such as yeast cells and the like. Furthermore, biologically-relevant microparticles can also include biologically-relevant polymers such as nucleic acids and proteins, or complexes thereof. In addition, industrial particles may be for example, organic or inorganic polymer materials, metals or the like. Organic polymer materials can include polystyrene, styrenedivinyl benzene, polymethyl methacrylate or the like. Inorganic polymer materials can include glass, silica, magnetic materials and the like. Metals can include gold colloids, aluminum and the like. With respect to the shape of these microparticles, it is generally common to have a spherical form, but the shape may be non-spherical, and in addition, the size and mass thereof is not particularly limited.

Advantageous Effects of Invention

According to the present technology, it is possible to provide a microparticle measurement device that can deliver a liquid that is used in the analysis of microparticles in a stable manner.

DESCRIPTION OF EMBODIMENTS

Hereinafter, preferable embodiments for implementing the present technology will be described with reference to the drawings. Additionally, the embodiments that are described below show a representative example of an embodiment of the present technology, and the scope of present technology should not be narrowly interpreted as a result of these embodiments. The description will be given in the following order.

1. Configuration of Microparticle Measurement Device
(1) Microchip
(2) Liquid Delivery System
(3) Optical Detection System
(4) Isolation System
(5) Control Unit
2. Action of Microparticle Measurement Device
3. Modification Examples 1. Configuration of Microparticle Measurement Device FIGS. 1 and 2 are schematic diagrams that describe a configuration of a liquid delivery system in a microparticle measurement device 1 (hereinafter, also referred to as a "flow cytometer 1") according to the present technology that is configured as a microchip type flow cytometer.

A microparticle measurement device of the present technology is provided with a plurality of first tank units to which a liquid is supplied from the outside, and which are respectively connected in parallel, and a bulb unit that is connected to the plurality of first tank units, and which switches to a state in which it is possible to deliver the liquid to a flow channel through which microparticles flow.

(1) Microchip

Figure 1:
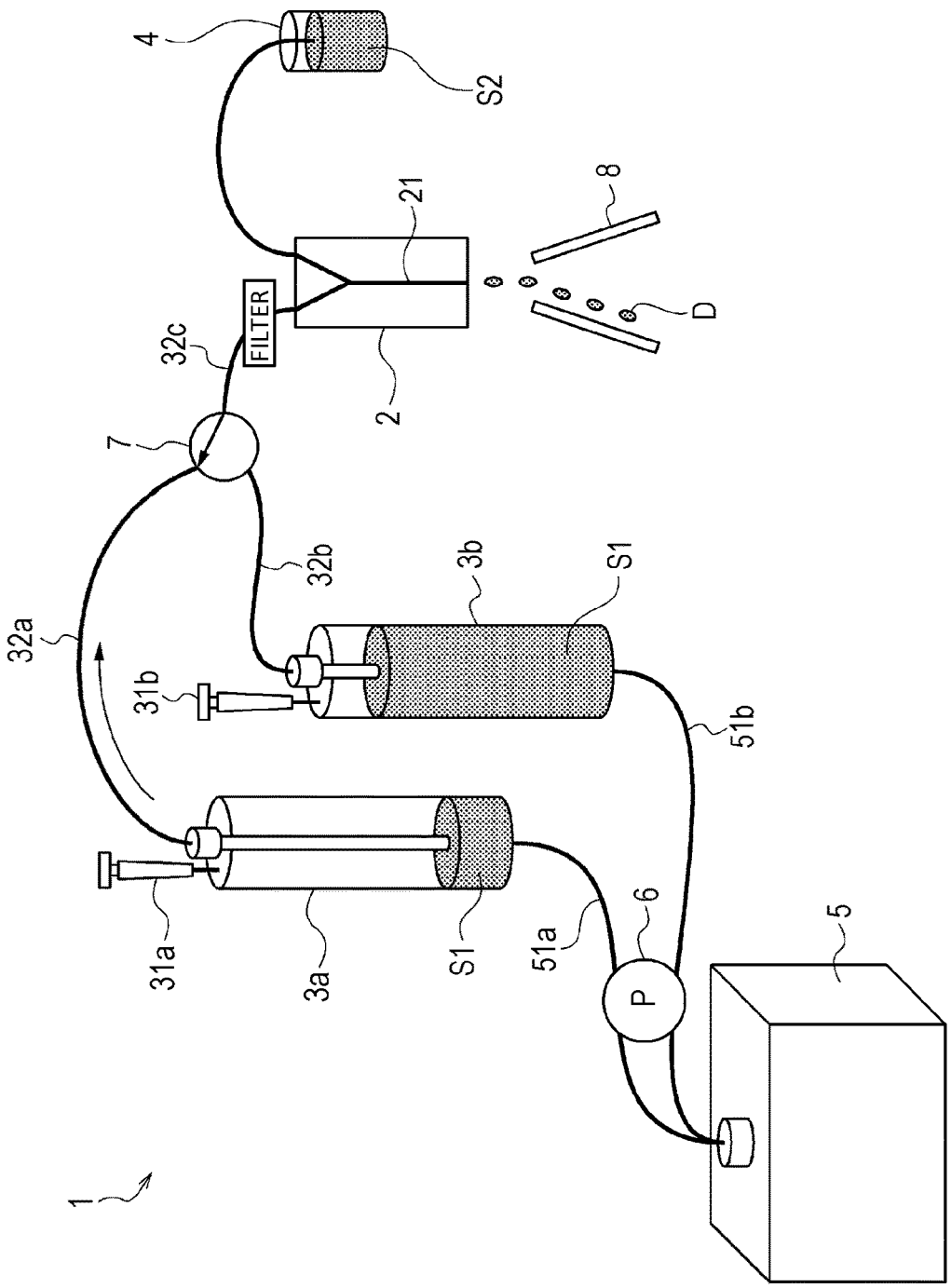
FIG. 1 is a schematic diagram for describing a configuration and an action of a liquid delivery system in a microparticle measurement device according to the present technology.
Figure 2:
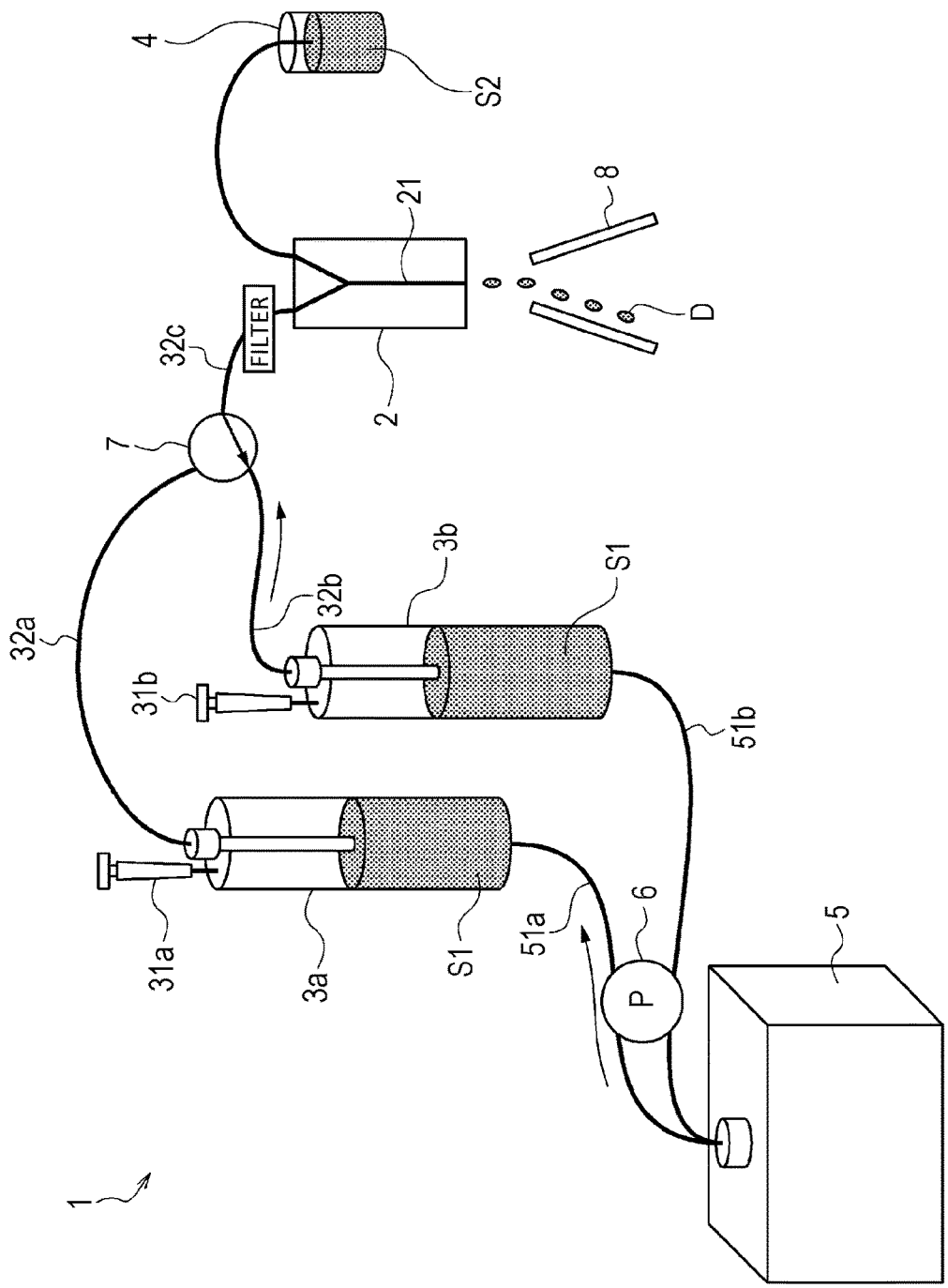
FIG. 2 is a schematic diagram for describing an action in the microparticle measurement device shown in FIG. 1 that differs from the action of FIG. 1.

In the flow cytometer 1 that is exemplified in FIG. 1, a flow channel 21 into which a sheath liquid S1 and a sample liquid S2, which includes microparticles that are a target of the measurement of optical analysis or the like, are introduced, is formed on a disposable microchip 2. The flow channel 21 also forms the site of the optical analysis of the microparticles that flow therethrough. In addition, the flow channel 21 is formed so that the sample liquid S2 that is introduced therein is interposed between the sheath liquid S1 that is introduced therein. Further, the laminar flow of the sample liquid S2 that is introduced forms a three-dimensional laminar flow in which the laminar flow is interposed between the laminar flow of the sheath liquid S1 that is introduced, and microparticles in the three-dimensional laminar flow are disposed in one row.

An orifice is provided at one end of the flow channel 21 that is formed in the microchip 2, and the three-dimensional laminar flow that is formed by the flow channel 21 becomes a fluid stream and is ejected from the orifice.

The fluid stream that is emitted from the orifice is converted into liquid droplets by vibrations that are applied to the entire microchip 2 or the orifice by a chip vibration unit such as a piezoelectric vibrator, and liquid droplets D are formed.

The microchip 2 is formed by a substrate on which the flow channel 21 is formed. The substrate is formed by for example, glass or various resin materials such as PC, PMMA, PE, PP, PS and polydimethylsiloxane (PDMS).

The formation of the flow channel 21 in the substrate can be performed using for example, wet etching or dry etching of a glass substrate, injection molding of a thermoplastic resin material, nanoimprinting or machining of a resin substrate or the like. In addition, the microchip 2 can be formed by sealing a substrate in which a flow channel is formed with a substrate of the same quality of material or a different quality of material.

(2) Liquid Delivery System

The sheath liquid S1 that is accommodated in first tank units 3a and 3b (hereinafter, also given the reference symbol 3 in which reference symbols 3a and 3b are combined) that are provided inside the device 1 and the sample liquid S2 that is accommodated in a sample liquid tank 4 are delivered to the flow channel 21 of the abovementioned microchip 2. The sheath liquid S1 and the sample liquid S2 are for example, introduced from filling holes (inlets) that are provided in the microchip 2 to be continuous with the flow channel 21.

In the present technology, a plurality of first tank units 3 (two in FIG. 1) are provided, and the first tank units 3 are respectively connected in parallel. In addition, each of the first tank units 3a and 3b is configured so that the sheath liquid S1 is provided from the outside. For example, the plurality of first tank units 3a and 3b may be configured so as to be connected to a second tank unit 5 that is provided on the outside of the flow cytometer 1, and the sheath liquid S1 may be supplied to the first tank units 3a and 3b from the second tank unit 5.

It is preferable that the supply of the sheath liquid S1 from the second tank unit 5 to each of the first tank units 3a and 3b be performed by a single supply pump unit 6 that is provided between each of the first tank units 3a and 3b and the second tank unit 5.

The supply pump unit 6 sends the sheath liquid S1 inside the second tank unit 5 to supply channels 51a and 51b, and supplies the sheath liquid S1 to the first tank units 3a and 3b through the supply channels 51a and 51b.

In the present technology, a single bulb unit 7 that switches to a state in which it is possible to deliver the sheath liquid S1 to the flow channel 21 of the microchip 2 is connected to the plurality of first tank units 3.

Among the plurality of first tank units 3, the bulb unit 7 sets a portion of first tank units 3a to a state in which it is possible to deliver the sheath liquid S1, sets other first tank units 3b to a state in which liquid delivery is ceased, and can switch between the delivery of the sheath liquid S1 and the cessation of the delivery thereof.

In the flow cytometer 1 that is shown in FIG. 1 and is provided with two first tank units 3a and 3b, one first tank unit 3a is set to a state (bulb open state) in which it is possible to deliver the sheath liquid S1, and the other first tank unit 3b is set to a state (bulb closed state) in which liquid delivery is ceased. In this case, it is preferable that a three-way valve be used as the bulb unit 7.

It is possible to respectively provide pressurization units 31a and 31b that increase the pressure of the first tank units 3a and 3b in the plurality of first tank units 3a and 3b. By increasing the pressure of the sheath liquid S1 that is accommodated in the first tank unit 3 using the pressurization units 31a and 31b, it is possible to deliver the sheath liquid S1 to the flow channel 21 of the microchip 2 through sheath liquid S1 liquid delivery channels 32a, 32b and 32c.

A filter unit, as shown in FIGS. 1 and 2, may be provided in the sheath liquid 51 liquid delivery channel 32c that is between the bulb unit 7 and the flow channel 21 (of the microchip 2). Using the filter unit, it is possible to prevent foreign particles and dust that can be included in the sheath liquid S1 from flowing into the flow channel 21.

In the present technology, it is preferable that the above-mentioned supply pump unit 6 and the bulb unit 7 be configured so as to be mutually driven in conjunction. This will be described more specifically below.

Firstly, the sheath liquid S1 is supplied from the second tank unit 5 to the plurality of first tank units 3a and 3b by driving the supply pump unit 6. Among the plurality of first tank units 3a and 3b, the bulb unit 7 is opened in order to make liquid delivery of the sheath liquid S1 from the first tank unit 3a to which the sheath liquid S1 is supplied, possible. Further, the sheath liquid S1 is delivered from the first tank unit 3a to the flow channel 21 of the microchip 2 (refer to an arrow that follows the liquid delivery channel 32a in FIG. 1). At this time, the bulb unit 7 is closed with respect to a first tank unit 3b that is different from the first tank unit 3a that is performing liquid delivery of the sheath liquid S1, and set to a state in which liquid delivery is ceased.

When the residual quantity of sheath liquid of the first tank unit 3a that is performing liquid delivery of the sheath liquid S1 becomes low or runs out, the open and closed state of the bulb unit 7 is switched so that liquid delivery of the sheath liquid S1 from a different first tank unit 3b, in which the sheath liquid S1 has been replenished, becomes possible. Along with this, liquid delivery of the sheath liquid S1 from the abovementioned different first tank unit 3b to the flow channel 21 of the microchip 2 is initiated (refer to an arrow that follows the liquid delivery channel 32b in FIG. 2).

In addition, the bulb unit 7 is closed with respect to the first tank unit 3a in which the residual quantity of sheath liquid has become low so that liquid delivery of the sheath liquid S1 enters a ceased state, and as shown in FIG. 2, the supply of the sheath liquid S1 from the second tank unit 5 to the first tank unit 3a is initiated by driving the supply pump unit 6 (refer to an arrow that follows the supply channel 51a in FIG. 2).

In this manner, with a first tank unit 3 that is set to a state (an open state of the bulb unit 7) in which liquid delivery of the sheath liquid S1 is possible and a first tank unit 3 that is set to a state (a closed state of the bulb unit 7) in which liquid delivery of the sheath liquid S1 is ceased, it is possible to configure such that the supply pump unit 6 is driven in correspondence with the open and closed state of the bulb unit 7.

The switching of the open and closed states of bulb unit 7 and the supply and cessation of supply of the supply pump unit 6 can be configured to be performed by a control unit that will be described later.

For example, the flow rate of the sheath liquid S1 that flows along the supply channels 51a and 51b, and the liquid delivery channels 32a, 32b and 32c, and the residual quantity of sheath liquid S1 that is accommodated in the second tank unit 5 and the first tank units 3 may be detected by providing a flow rate sensor and a residual quantity sensor in the liquid delivery system according to the present technology. The detected value of the flow rate of the sheath liquid S1 and the residual quantity inside the first tank unit 3 can be output to the control unit that will be described later.

Figure 3:
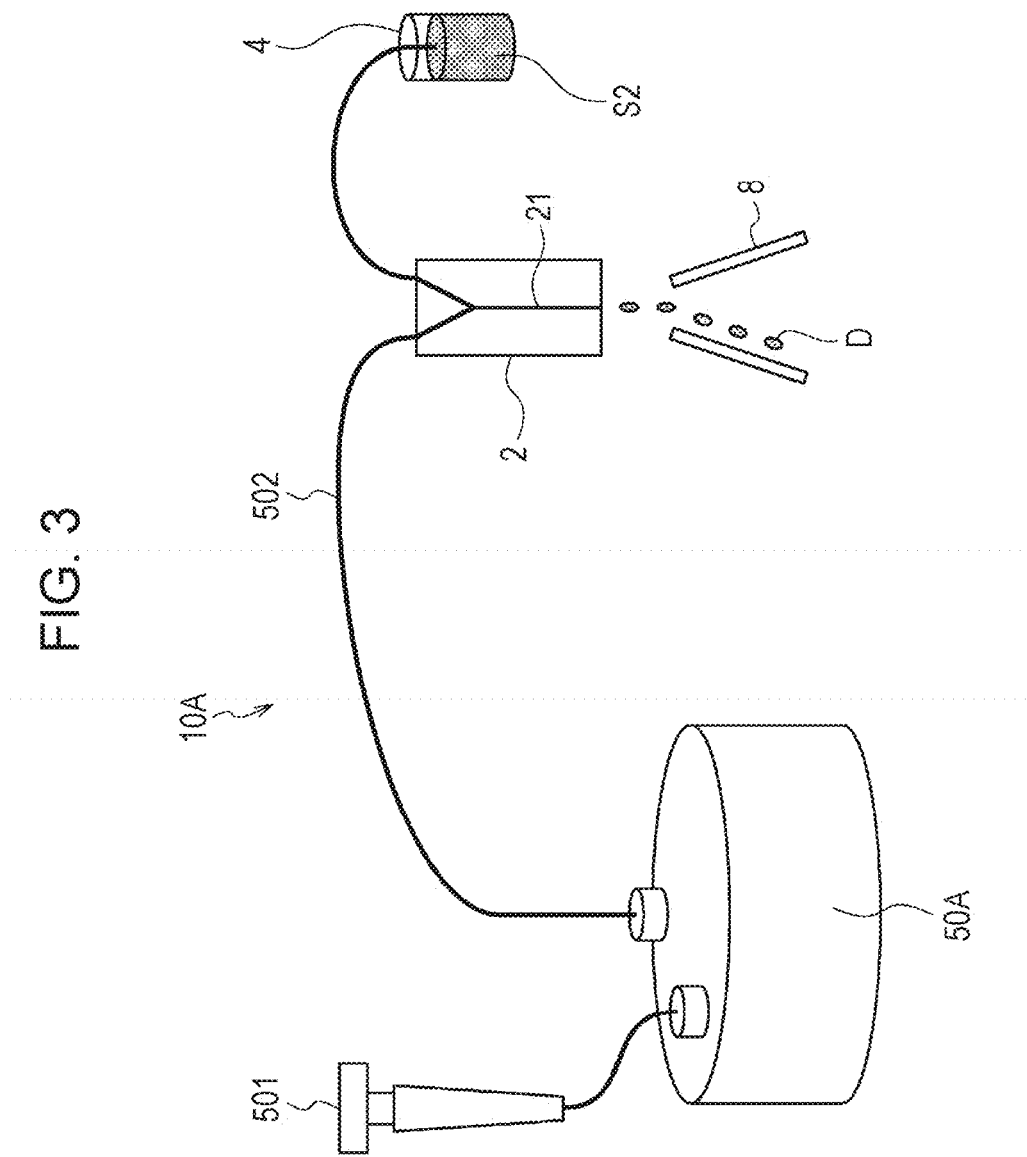
FIG. 3 is a schematic diagram for describing a configuration and an action of an example of a liquid delivery system in a microparticle measurement device that is compared with the microparticle measurement device according to the present technology.
Figure 4:
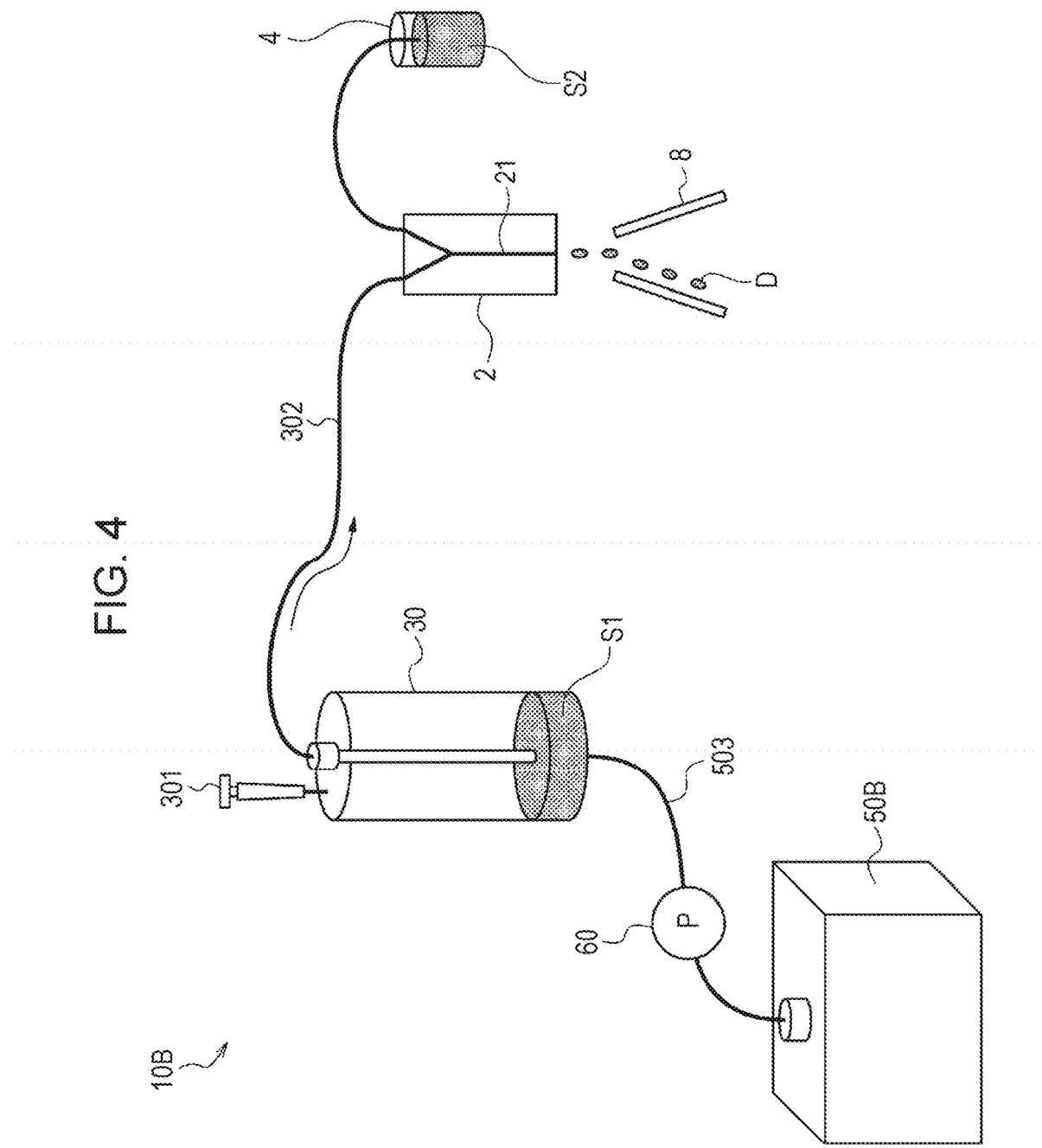
FIG. 4 is a schematic diagram for describing a configuration and an action of a different example of a liquid delivery system in a microparticle measurement device that is compared with the microparticle measurement device according to the present technology.
Figure 5:
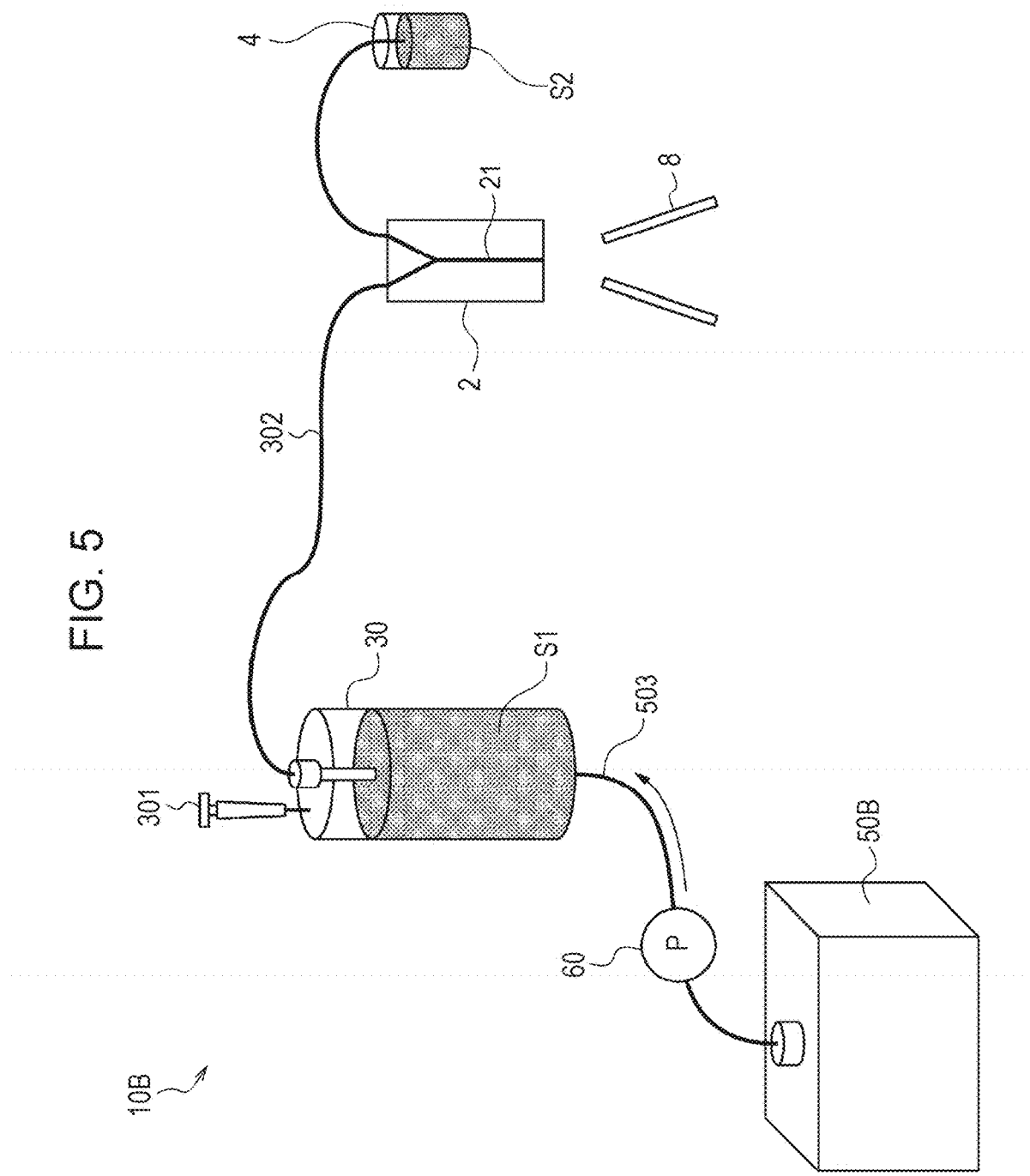
FIG. 5 is a schematic diagram for describing an action in the microparticle measurement device shown in FIG. 4 that differs from the action of FIG. 4.

Incidentally, before discovering the configuration of the liquid delivery system according to the present technology, the inventors of the present technology considered the configurations of other liquid delivery systems such as those shown in FIGS. 3 to 5.

A microparticle measurement device 10A that is provided with the liquid delivery system shown in FIG. 3 is configured so as to deliver a sheath liquid to a flow channel 21 of a microchip 2 directly from an external sheath liquid tank 50A that is outside the device using a liquid delivery channel 502. The external sheath liquid tank 50A is a tank that has a large capacity in comparison with the first tank units 3 that are provided inside the device in the abovementioned liquid delivery system according to the present technology. In addition, the external sheath liquid tank 50A has a configuration in which pressure from a pressurization unit 501 is directly applied thereto. Therefore, a specially-shaped lid is provided so that the external sheath liquid tank 50A can withstand high pressures, the opening and closing of the lid is not easy, and has a complex configuration when the external sheath liquid tank 50A is being replenished with sheath liquid or being exchanged with another external sheath liquid tank.

In the liquid delivery system shown in FIG. 3, it became clear that problems such as the handling of the external sheath liquid tank 50A being troublesome and the concern of foreign matter and dust becoming mixed in when a commercially available sheath liquid is transferred to the external sheath liquid tank 50A, arose. Furthermore, since the external sheath liquid tank 50A has a large capacity, there is a tendency for the vibrations that are generated at the time of an increase in pressure or suctioning of the sheath liquid by the pressurization unit 501 to be transmitted to the liquid droplets D that are ejected from the microchip 2, and it became clear that a problem in which the formation of the liquid droplets D became unstable arose. In particular, this problem accompanies changes in the residual quantity of sheath liquid and the position of the fluid level of the external sheath liquid tank 50A, and was caused by large changes in pressure.

In view of the problems that arise in the liquid delivery system shown in FIG. 3, the inventors of the present technology considered a microparticle measurement device 10B that is provided with a configuration of the liquid delivery system shown in FIG. 4. The liquid delivery system shown in FIG. 4 is configured so that a sheath liquid S1 is supplied from an external sheath liquid tank 50B that is outside the device to an internal sheath liquid tank 30, which is inside the device, through a supply channel 503 using a supply pump unit 60. Further, this liquid delivery system is configured so that the sheath liquid S1 that is supplied to the internal sheath liquid tank 30 is delivered to a flow channel 21 of a microchip 2 through the liquid delivery channel 302 by a pressurization unit 301 (refer to an arrow that follows the liquid delivery channel 302 in FIG. 4).

In the liquid delivery system shown in FIG. 4, it is possible to configure such that it is unlikely that changes in the residual quantity of sheath liquid S1 inside the external sheath liquid tank 50B, changes in the pressure that is applied to the sheath liquid S1, and the like, have an effect by providing the internal sheath liquid tank 30.

However, there was a tendency for the shape of the liquid droplets D that are ejected from the microchip 2 to collapse due to the effect of pressure that is applied to the external sheath liquid tank 50B and the sheath liquid therein while the sheath liquid S1 in the internal sheath liquid tank 30 is being replenished from the external sheath liquid tank 50B. Therefore, as shown in FIG. 5, it became clear that it was necessary to cease the ejection (sorting) of liquid droplets D from the microchip 2 while the sheath liquid S1 in the internal sheath liquid tank 30 is being replenished (refer to an arrow that follows the supply channel 503 in FIG. 5). This was particularly a problem in a case in which sorting was performed over a long period of time.

In the manner described above, as a result of a thorough investigation of liquid delivery systems, the inventors of the present technology conceived of a configuration in which a plurality of internal sheath liquid tanks (first tank units 3) to which sheath liquid S1 is supplied from the outside are provided, and the plurality of first tank units 3 are respectively connected in parallel. Further, by providing the plurality of first tank units 3 and a bulb unit 7 that switches to a state in which it is possible to deliver the sheath liquid S1 to the flow channel 21 of the microchip 2, the inventors of the present technology discovered that it is possible to deliver a liquid such as the sheath liquid S1 that is accommodated in the first tank units 3 to the flow channel 21 in a stable manner.

In the microparticle measurement device 1 that is provided with the liquid delivery system according to the present technology, by providing a plurality of first tank units 3 that are connected in parallel, it is unlikely that changes in the residual quantity of sheath liquid S1 inside the second tank unit 5 that is outside, changes in the pressure that is applied to the sheath liquid, and the like, have an effect, and it is possible to shield the plurality of first tank units 3a and 3b from vibrations that are generated by the second tank unit 5.

In addition, in the microparticle measurement device 1 according to the present technology, since a plurality of first tank units 3 are provided, it is possible to reduce the capacity (miniaturization) of the first tank units 3a and 3b in comparison with the second tank unit 5. Therefore, pressure changes that are caused by a liquid delivery pump for delivering liquid from the first tank units 3a and 3b to the flow channel 21 are small, and it is possible to perform the formation of liquid droplets D in a stable manner.

Furthermore, in the microparticle measurement device 1 according to the present technology, it is possible to perform switching between liquid delivery of the sheath liquid S1 from the first tank units 3 to the flow channel 21 and supply of the sheath liquid S1 from the outside to the first tank units 3 using the configuration of the abovementioned plurality of first tank units 3 and the bulb unit 7. As a result, it is possible to perform liquid delivery of the sheath liquid S1 to the flow channel 21 in a stable manner.

Additionally, in the microparticle measurement device 1 according to the present technology, it is possible to provide an optical detection system, an isolation system and a control unit as described later, in the same manner as microparticle measurement devices of the related art (which include a microparticle analysis device, a microparticle isolation device and a cell sorter).

(3) Optical Detection System

In the same manner as that of microparticle measurement devices of the related art, the measurement of the optical characteristics of the microparticles that flow through the flow channel 21 may be performed by an optical detection system.

The optical detection system irradiates the microparticles that flow through the flow channel 21 in a predetermined position of the flow channel 21 with excitation light such as laser light, detects fluorescence, scattered light and the like that is generated from the microparticles, and converts the result into an electrical signal.

More specifically, the optical detection system is configured by a laser light source, an irradiation system that is formed from a collecting lens for collecting laser light and irradiating the microparticles with laser light, a dichromatic mirror, a band pass filter and the like, and a detection system that detects light that is generated from the microparticles due to the irradiation of laser light. The detection system for example, can be configured by an area imaging element such as a PMT (photomultiplier tube), a CCD or a CMOS element.

Measurement target light that is detected by the detection system is light that is generated from the microparticles due to the irradiation of measurement light, and for example, can be set as forward scattered light and lateral scattered light, scattered light such Rayleigh scattering and Mie scattering and fluorescence. This measurement target light is converted into electrical signals, and output to the control unit which will be described later.

In the microparticle measurement device 1, the optical detection system may for example, be replaced by an electrical or a magnetic detection unit. In a case of electrical or magnetic detection of the characteristics of microparticles, microelectrodes are arranged on both sides of the flow channel 21 so as to face one another, and resistance values, content values (capacitance values), inductance values, impedance, changes in the values of the electrical field, magnetization, changes in the magnetic field, changes in the magnetic field or the like between the electrodes are measured.

(4) Isolation System

It is possible to set a configuration that isolates the microparticles that are emitted from the orifice of the microchip 2 to have the same configuration as microparticle measurement devices of the related art.

More specifically, it is possible to configure so as to provide a charging unit that applies an electric charge to the liquid droplets D that includes the microparticles that are discharged from the orifice, a pair of deflector plates 8 that are arranged along a movement direction of liquid droplets D that are discharged from the orifice, and positioned so as to face one another with the liquid droplets D interposed therebetween, and a plurality of recovery containers that receive the liquid droplets D that contain microparticles.

The pair of deflector plates 8 are configured to include electrodes that control the movement direction of the liquid droplets D due to an electrical acting force with the electric charge that is applied to the liquid droplets D by the charging unit. In addition, the deflector plates 8 control the trajectory of a fluid stream that is emitted from the orifice using an electrical acting force with the electric charge that is applied to the fluid stream. Depending on the presence or absence of an electrical acting force between the deflector plates 8 or the intensity thereof, the liquid droplets D that are discharged from the orifice are lead to one of the recovery containers among the plurality of recovery containers and recovered.

(5) Control Unit

In addition to the above described configuration, the flow cytometer 1 is provided with a data analysis unit for determination of the optical characteristics of the microparticles and a control unit that common flow cytometers are provided with.

The control unit is for example, configured by general-purpose computer that is provided with a CPU, memory, a hard disk and the like.

The control unit in the present technology performs control of the switching of the open and closed states of the abovementioned bulb unit 7, and switching of the supply and cessation of supply of the supply pump unit 6.

Additionally, a configuration in which a different control unit is respectively provided for the liquid delivery system, the optical detection system and the isolation system, and control is respectively performed by these control units, may be used.

2. Action of Microparticle Measurement Device

Next, a method for delivering a liquid that is used in the analysis of microparticles using the microparticle measurement device 1 of the present technology will be described.

Firstly, the microparticle measurement device 1 of the present technology supplies the sheath liquid S1 from the second tank unit 5 to the first tank units 3. Thereafter, in addition to setting the bulb unit 7 to an open state with respect to a first tank unit 3a to which the sheath liquid S1 has been supplied, liquid delivery of the sheath liquid S1 from the first tank unit 3a to the flow channel 21 of the microchip 2 is performed.

The liquid delivery of the sheath liquid S1 to the flow channel 21 may be performed after the sheath liquid S1 in all of the plurality of first tank units 3 have been replenished from the second tank unit 5, or may be performed after the sheath liquid S1 in a portion of the first tank units 3 among the plurality of first tank units 3 have been replenished.

In a case in which liquid delivery to the flow channel 21 is performed from a first tank unit 3 in which the replenishment of the sheath liquid S1 has been completed after the sheath liquid S1 in a portion of the first tank units 3 among the plurality of first tank units 3a and 3b has been replenished, the supply of the sheath liquid S1 from the second tank unit 5 is performed with respect to a first tank unit 3b that is different to the abovementioned first tank unit 3a.

In addition to setting the bulb unit 7 to a closed state with respect to the first tank unit 3a when the residual quantity of sheath liquid in the first tank unit 3a that is delivering the sheath liquid S1 to the flow channel 21 has become low, the bulb unit 7 is set to an open state with respect to the different first tank unit 3b in which the sheath liquid S1 is replenished. At the same time, by driving the supply pump unit 6, the sheath liquid S1 is supplied from the second tank unit 5 to first tank unit 3a in which the residual quantity of sheath liquid has become low.

In this manner, the supply of the sheath liquid S1 from the second tank unit 5 with respect to the first tank units 3 that are in a liquid delivery state, is ceased, and the supply pump unit 6 and bulb unit 7 are driven in conjunction so as to supply the sheath liquid S1 from the second tank unit 5 with respect to first tank units 3 that are in a non-liquid delivery state.

Additionally, the liquid delivery method in the microparticle measurement device 1 according to the present technology can be stored as a program on a hardware resource that is provided with the abovementioned control unit and a recording medium (such as a non-volatile memory (USB memory or the like), an HDD, a CD or the like), and realized using the control unit.

3. Modification Examples

In the abovementioned embodiment, an example of a configuration in which two first tank units 3a and 3b are provided is shown, but it is possible to provide 3 or more first tank units. In this case, a configuration in which liquid delivery from the first tank units to the flow channel is performed only from a single first tank unit may be used, and a configuration in which liquid delivery to the flow channel is performed from two or more first tank units at the same time may also be used. Microparticle measurement device of either case act so as to deliver liquid from the first tank units to the flow channel and supply a liquid such as a sheath liquid from the outside to first tank units other than those mentioned above at the same time.

For example, in a case in which a microparticle measurement device is provided with three first tank units, the microparticle measurement device 1 may have a configuration of being set to perform liquid delivery from a single first tank unit, and supply a sheath liquid from the outside to the two first tank units other than the first tank unit that is delivering liquid.

In addition, in the abovementioned embodiment, an example of a configuration of being provided with a single supply pump unit 6 that supplies the sheath liquid S1 from the second tank unit 5 to the plurality of first tank units 3 is shown, but a plurality of supply pump units 6 may be provided so as to respectively supply the sheath liquid S1 to the plurality of first tank units 3.

Furthermore, in the abovementioned embodiment, an example of a configuration in which a single bulb unit that is connected to the plurality of first tank units 3, and which switches to a state in which it is possible to deliver the sheath liquid S1 to the flow channel 21 is shown, but a plurality of bulb units may be provided so as to respectively correspond to the plurality of first tank units 3.

The microparticle measurement device as in the present technology may adopt the following configurations.

(1) A microparticle measurement device including a plurality of first tank units to which a liquid is supplied from the outside, and which are respectively connected in parallel, and a bulb unit that is connected to the plurality of first tank units, and which switches to a state in which it is possible to deliver the liquid to a flow channel through which microparticles flow.

(2) The microparticle measurement device according to (1), in which the plurality of first tank units is connected to a second tank unit that is on the outside, and the liquid is supplied from the second tank unit.

(3) The microparticle measurement device according to (2), further including a supply pump unit that supplies the liquid from the second tank unit to the plurality of first tank units.

(4) The microparticle measurement device according to (3), in which the bulb unit and the supply pump unit are driven in conjunction.

(5) The microparticle measurement device according to (3) or (4), in which the single bulb unit and the single supply pump unit are provided.

(6) The microparticle measurement device according to any one of (3) to (5), in which among the plurality of first tank units, the supply pump unit ceases the supply of the liquid to first tank units which are in a liquid delivery state with respect to the flow channel, and supplies the liquid to first tank units which are in a ceased liquid delivery state with respect to the flow channel.

(7) The microparticle measurement device according to any one of (1) to (6), further including a filter unit in a liquid delivery channel of the liquid between the bulb unit and the flow channel.

(8) The microparticle measurement device according to any one of (1) to (7), in which the first tank unit is provided inside the device.

(9) The microparticle measurement device according to any one of (1) to (8), in which the flow channel is provided on a microchip.

(10) A liquid delivery method in a microparticle measurement device, including setting a portion of tank units to a state in which the liquid is delivered to a flow channel through which microparticles flow using a bulb unit, among a plurality of first tank units to which a liquid is supplied from the outside, and which are respectively connected in parallel; setting tank units other than the portion of tank units to a state in which liquid delivery of the liquid to the flow channel is ceased; and supplying the liquid to the tank units other than the portion of tank units from the outside during a period when the liquid is being delivered from the portion of tank units to the flow channel.

REFERENCE SIGNS LIST 1 microparticle measurement device (flow cytometer)
2 microchip
21 flow channel
3a, 3b first tank unit
31a, 31b pressurization unit
32a, 32b, 32c liquid delivery channel
4 sample liquid tank
5 second tank unit
51a, 51b supply channel
6 supply pump unit
7 bulb unit
S1 sheath liquid
S2 sample liquid
D liquid droplets

The invention claimed is:

1. A microparticle measurement device, comprising:
a plurality of first tank units configured to be supplied with a liquid from a second tank unit;
a valve unit connected to the plurality of first tank units, and which is configured to switch to a state in which the liquid is delivered to a flow channel through which microparticles flow; and
a supply pump unit between each of the plurality of first tank units and the second tank unit, and configured to supply the liquid from the second tank to the plurality of first tank units.

2. The microparticle measurement device according to claim 1, wherein the valve unit is further configured to be switched and the supply pump unit is further configured to be driven in conjunction with each other.

3. The microparticle measurement device according to claim 1, wherein a single valve unit and a single supply pump unit are provided.

4. The microparticle measurement device according to claim 1, wherein the supply pump unit is further configured to cease the supply of the liquid to a first portion of the plurality of first tank units which are in a liquid delivery state with respect to the flow channel, and supply the liquid to a second portion of the plurality of first tank units which are in a ceased liquid delivery state with respect to the flow channel, wherein the second portion is other than the first portion.

5. The microparticle measurement device according to claim 1, further comprising:
a filter unit in a liquid delivery channel of the liquid between the valve unit and the flow channel.

6. The microparticle measurement device according to claim 1, further comprising:
a pressurization unit for each of the plurality of first tank units.

7. The microparticle measurement device according to claim 1, wherein the flow channel is on a microchip.

8. The microparticle measurement device according to claim 1, wherein the supply pump unit is further configured to supply the liquid from the second tank to the plurality of first tank units through a supply channel connected to each of the plurality of first tank units.

9. A liquid delivery method, comprising:
in a microparticle measurement device:
setting a first portion of a plurality of first tank units to a state in which the liquid is delivered to a flow channel through which microparticles flow using a valve unit;
setting a second portion of the plurality of first tank units other than the first portion of the plurality of first tank units to a state in which liquid delivery of the liquid to the flow channel is ceased; and
supplying the liquid to the second portion of the plurality of first tank units from a second tank unit during a period in which the liquid is being delivered from the first portion of the plurality of first tank units to the flow channel, wherein the liquid is supplied to the second portion of the plurality of first tank units from the second tank unit through a supply pump unit, between each of the plurality of first tank units and the second tank unit.

\* \* \* \* \*